(12) United States Patent
Domina (10) Patent No.: US 12,402,904 B2
(45) Date of Patent: Sep. 2, 2025

(54) SCISSOR CLAMP (71) Applicant: Michael Domina, El Paso, TX (US)

(72) Inventor: Michael Domina, El Paso, TX (US)

(*) Notice: Subject to any disclaimer, the term of this patent is extended or adjusted under 35 U.S.C. 154(b) by 270 days.

(21) Appl. No.: 18/199,836

(22) Filed: May 19, 2023

(65) Prior Publication Data

US 2024/0130725 A1 Apr. 25, 2024
US 2024/0225636 A9 Jul. 11, 2024

Related U.S. Application Data

(60) Provisional application No. 63/343,693, filed on May 19, 2022.

(51) Int. Cl.
*A61B 17/04* (2006.01)
*A61B 17/28* (2006.01)
*A61B 17/3201* (2006.01)

(52) U.S. Cl.
CPC .......... *A61B 17/28* (2013.01); *A61B 17/0487* (2013.01); *A61B 17/3201* (2013.01)

(58) Field of Classification Search
CPC .. A61B 17/28; A61B 17/0487; A61B 17/3201
See application file for complete search history.

(56) References Cited

U.S. PATENT DOCUMENTS

| | | | | |
|---|---|---|---|---|
| 5,254,129 | A * | 10/1993 | Alexander | A61B 17/295 606/174 |
| 5,843,121 | A * | 12/1998 | Yoon | A61B 17/12013 606/205 |
| 6,051,004 | A * | 4/2000 | Gill | A61B 17/062 606/147 |
| 6,976,992 | B2 * | 12/2005 | Sachatello | A61B 17/062 606/208 |
| 9,277,932 | B2 * | 3/2016 | Slater | A61B 17/3201 |
| 12,167,846 | B2 * | 12/2024 | Murray | A61B 17/076 |
| 2010/0298852 | A1 * | 11/2010 | Slater | A61B 17/320016 606/205 |
| 2018/0168568 | A1 * | 6/2018 | Ali | A61B 17/0467 |

* cited by examiner

*Primary Examiner* — Julian W Woo
(74) *Attorney, Agent, or Firm* — The Rapacke Law Group, P.A.

(57) ABSTRACT

A suture scissor clamp has a first and second shanks having a first and second finger rings and connected to a first and second jaws, respectively. The first shank is connected to the second shank by crossing the second shank such that when the first ring and the second ring are moved towards each other, the first jaw and the second jaw move towards each other. A first blade is connected to the first jaw and a second blade connected to the second jaw. The first blade and the second blade are not operable until after the first jaw and the second jaw are brought together. The first blade is inside or about the first jaw and the second blade is inside or about the second jaw. The first blade exits the first jaw towards the second blade and the second blade exits the second jaw towards the first blade when the first jaw and the second jaw are completely brought together and the first ring and the second ring are moved further towards each other.

17 Claims, 8 Drawing Sheets

SCISSOR CLAMP

CROSS-REFERENCE TO RELATED APPLICATIONS

The present application claims priority to U.S. Provisional Application No. 63/343,693 filed May 19, 2022, titled "DOMINA SCISSOR CLAMP" which is hereby incorporated by reference in its entirety.

TECHNICAL FIELD

Embodiments of the invention relate to a suture cutting device; and more particularly, to a suture scissor clamp that can be used in general surgery, abdominal surgery, and in the surgery of the vaginal canal and other surgical scenarios where the surgical field is narrow.

BACKGROUND

Medical doctors and surgeons routinely operate on patients in situations requiring precision and difficult handling and maneuvering of medical instruments. Any developments and improvements to the ease and speed of surgical operation assists the surgeons by lowering the chance of human error and reducing the time that the patient is exposed in surgery. The longer the time in surgery, the higher the chance of complications for a patient.

Currently, there is a need for a medical instrument that includes both a clamping and cutting function. This type of instrument would be particularly useful in vaginal surgery, abdominal surgery, and other surgeries and medical procedures that would benefit from an instrument that provides both a clamping and cutting function. An added benefit would be obtained from an instrument that provides a distance measurement from the tissue, which would inform how far the suture is being cut from the edge of your organ/tissue of interest.

SUMMARY OF THE INVENTION

This summary is provided to introduce a variety of concepts in a simplified form that is disclosed further in the detailed description of the embodiments. This summary is not intended for determining or limiting the scope of the claimed subject matter.

A suture scissor clamp comprises a first and second shanks having a first and second finger rings and connected to a first and second jaws, respectively. The first shank is connected to the second shank by crossing the second shank such that when the first ring and the second ring are moved towards each other, the first jaw and the second jaw move towards each other. A first blade is connected to the first jaw and a second blade connected to the second jaw. The first blade and the second blade are not operable until after the first jaw and the second jaw are brought together. The first blade is inside or about the first jaw and the second blade is inside or about the second jaw. The first blade exits the first jaw towards the second blade and the second blade exits the second jaw towards the first blade when the first jaw and the second jaw are completely brought together and the first ring and the second ring are moved further towards each other.

The novel suture scissor clamp's operation allows for precise and simple suture cutting in narrow and deep cavities of the body where ergonomics and fluidity of motion are typically challenged.

The foregoing general summary is intended to provide an overview or framework for understanding the nature and character of the embodiments disclosed herein. This summary is not intended to identify essential inventive concepts of the claimed subject matter or limit the scope of the claimed subject matter. Additional features and advantages of the embodiments disclosed herein will be set forth in the detailed description that follows, and in part will be clear to those skilled in the art from that description or recognized by practicing the embodiments described herein, including the detailed description that follows, the claims, and the appended drawings.

BRIEF DESCRIPTION OF THE DRAWINGS

A more complete understanding of the embodiments, and the attendant advantages and features thereof, will be more readily understood by references to the following detailed description when considered in conjunction with the accompanying drawings wherein.

The drawings are not necessarily to scale, and certain features and certain views of the drawings may be shown exaggerated in scale or in schematic in the interest of clarity and conciseness.

DETAILED DESCRIPTION

Reference will now be made in detail to the exemplary embodiment(s), examples of which is/are illustrated in the accompanying drawings. Whenever possible, the same reference numerals will be used throughout the drawings to refer to the same or like parts.

Before describing the exemplary embodiments, it is noted the embodiments reside primarily in combinations of components and procedures related to the apparatus. Accordingly, the apparatus components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

The specific details of the various embodiments described herein are used for demonstration purposes only, and no unnecessary limitation or inferences are to be understood therefrom. Furthermore, as used herein, relational terms, such as "first" and "second," "top" and "bottom," and the like, may be used solely to distinguish one entity or element from another entity or element without necessarily requiring or implying any physical or logical relationship, or order between such entities or elements.

In various embodiments, as shown in FIGS. 1A-3, a novel suture scissor clamp 10 is provided.

Figure 1A:
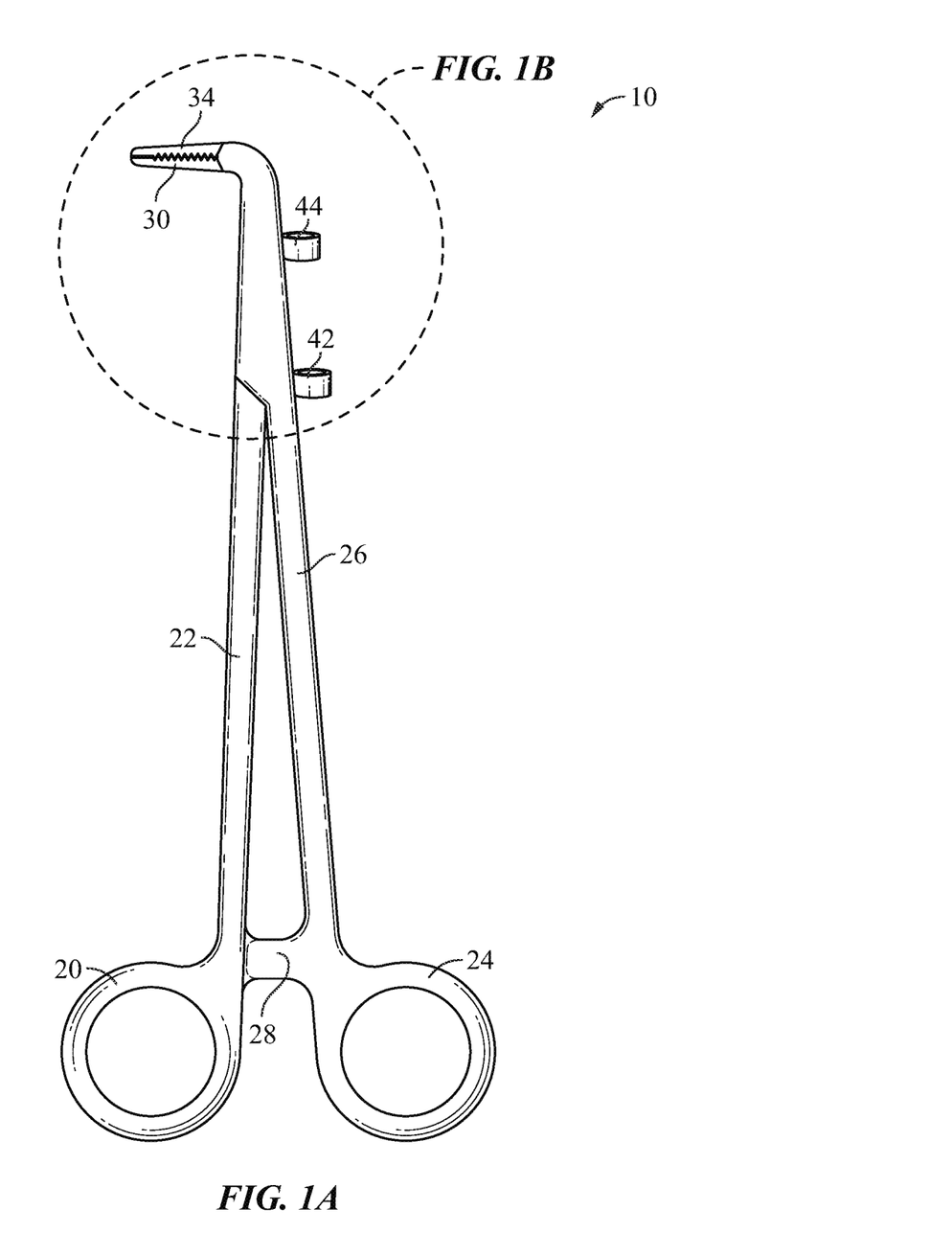
FIG. 1A illustrates an orthogonal view of a suture scissor clamp, according to some embodiments.
Figure 1B:
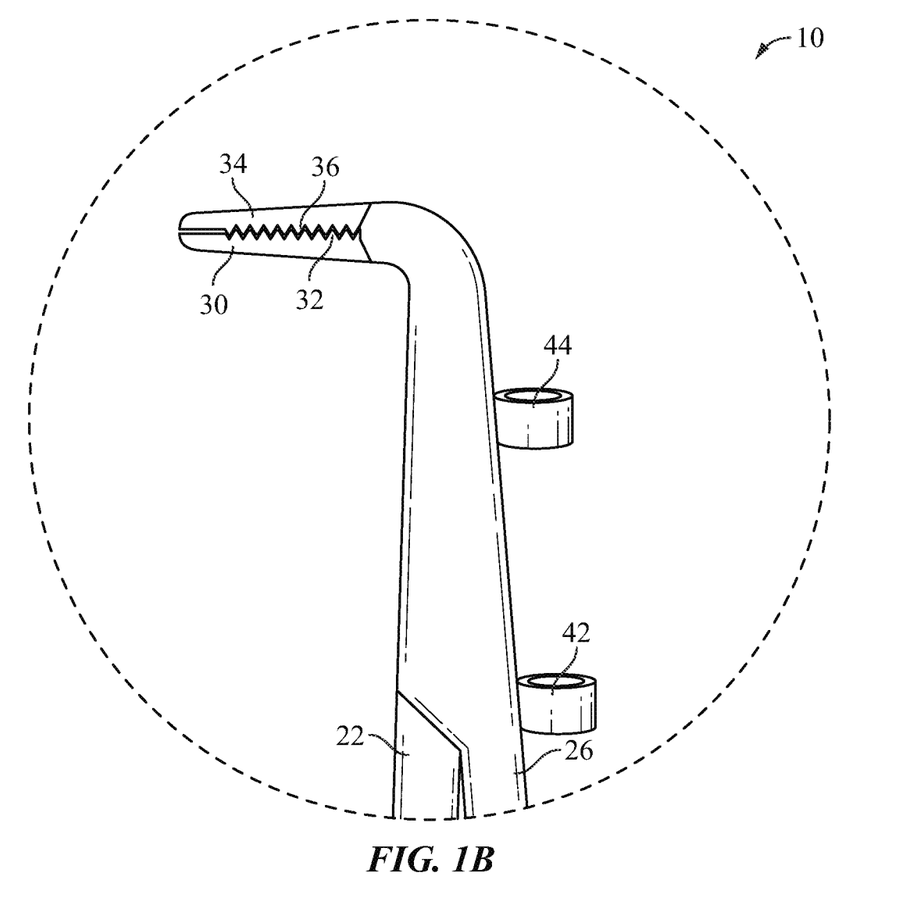
FIG. 1B shows an enlarged partial view of the suture scissor clamp in FIG. 1A.

FIGS. 1A and 1B illustrate the suture scissor clamp 10 in a closed configuration. In such closed configuration, the outer surface of the suture scissor clamp 10 is blunt. The suture scissor clamp 10 has a first finger ring 20 connected to a first shank 22, a second finger ring 24 connected to a second shank 26, locking ratchets 28 between the first and second finger rings 20 and 24, a bottom jaw 30 connected to the second shank 26, a top jaw 34 connected to the first shank 22, a first attachment loop 42, and a second attachment loop 44. According to one or more aspects, a suture scissor clamp has one, two, or more attachment loops, which can have one or more diameters, lengths, positions, and/or orientations. According to one or more aspects, a suture scissor clamp has one or more attachment conduits (or channels, cylinders, and/or the like) with internal openings, each having a circular, square, and/or other geometrical shapes, the same or different sizes, the same or different positions, spacings, and/or orientations, the same or different lengths, and/or the like.

The top and bottom jaws 34 and 30 can be at any angle (or no angle) with respect to the first and second shanks 22 and 26. Empirical experience demonstrates that an angle of the top and bottom jaws 34 and 30 of about 90 degrees with respect to the first and second shanks 22 and 26 is preferable for vaginal surgery. Empirical experience also demonstrates that the top and bottom jaws 34 and 30 should be no bigger than 1 or 2 centimeters in length and about 0.5 to 1 centimeters in width.

The suture scissor clamp 10, including the configuration of the first and second finger rings 20 and 24 and/or the configuration of the first and second shanks 22 and 26, can be designed for left-handed use, right-handed use, or for general (ambidextrous) use. General purpose scissors are left-handed or right-handed based on the way the blades are connected (for example, right-handed scissors in operation having the right-side blade going up and the left-side blade down). Note that, unlike the blades of general-purpose scissors, the top and bottom jaws 34 and 30 are configured to open and close below and above each other (retract and approach each other, or open and close an angle between the top and bottom jaws 34 and 30) without either of the top and bottom jaws 34 and 30 falling to the left or to the right of the other. Thus, left-handed, right-handed, and ambidextrous designs can focus on any other aspects of the suture scissor clamp 10, such as the shape and dimensions of the first and second finger rings 20 and 24, adding a tang or finger rest, adding a insert to the first and second finger rings 20 and 24, replacing the locking ratchets 28 with stoppers, and/or the like, without regard to the positions of and the connection between the first and second shanks 22 and 26.

FIG. 1B illustrates a magnified view of the upper-half portion of the suture scissor clamp 10, including the first and second shanks 22 and 26, the top and bottom jaws 34 and 30, and the first and second attachment loops 42 and 44. FIG. 1B also illustrates the bottom teeth 32 protruding from the bottom jaw 30 towards the top jaw 34, and the top teeth 36 protruding from the top jaw 334 towards the bottom jaw 30. The top teeth 36 and the bottom teeth 32 are configured to be spaced with respect to each other so that when the suture scissor clamp 10 is in closed configuration, there are no gaps or space between the top teeth 36, the bottom teeth 32, the top jaw 34, and/or the bottom jaw 30. The closed configuration with no gaps or space between the top teeth 36, the bottom teeth 32, the top jaw 34, and/or the bottom jaw 30 is based on the shapes, sizes, dimensions, angles, orientations, positions, and/or the like, of the top teeth 36, the bottom teeth 32, the top jaw 34, and/or the bottom jaw 30.

Figure 2:
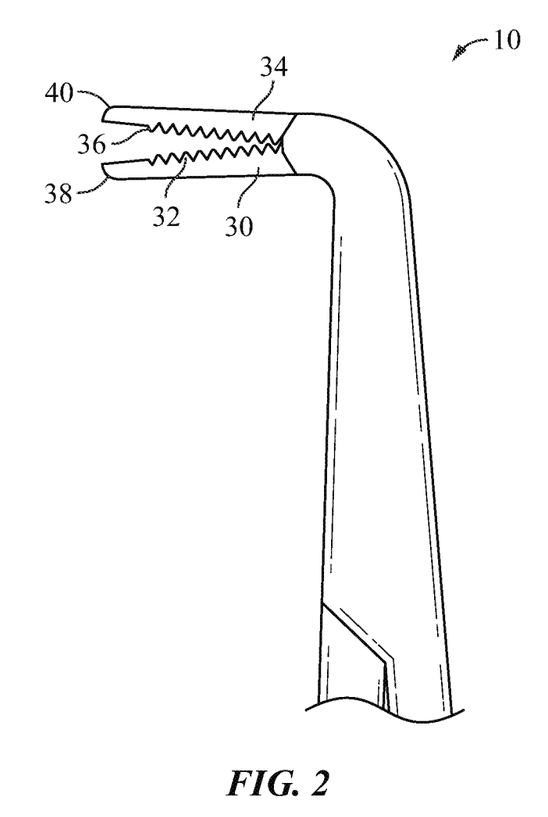
FIG. 2 shows an enlarged partial view of a suture scissor clamp, according to embodiments described herein.

FIG. 2 illustrates the top portion of the suture scissor clamp 10 in open configuration with the bottom jaw 30 having a bottom tip 38 and the top jaw 34 having a top tip 40. the bottom tip 38 has a bottom blade portion and the top tip has a top blade portion. The top blade portion and the bottom blade portion are confined to the inside of the suture scissor clamp 10, so no sharp ends are exposed while entering the vaginal or abdominal cavities.

Figure 3A:
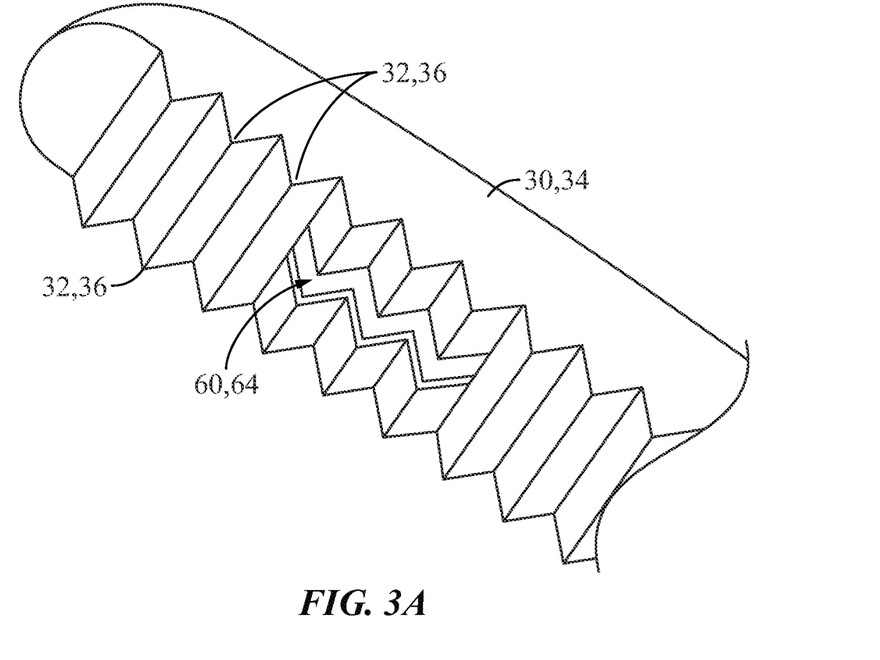
FIG. 3A show a perspective view of a jaw of a scissor clamp with a slot, according to one or more aspects.
Figure 3B:
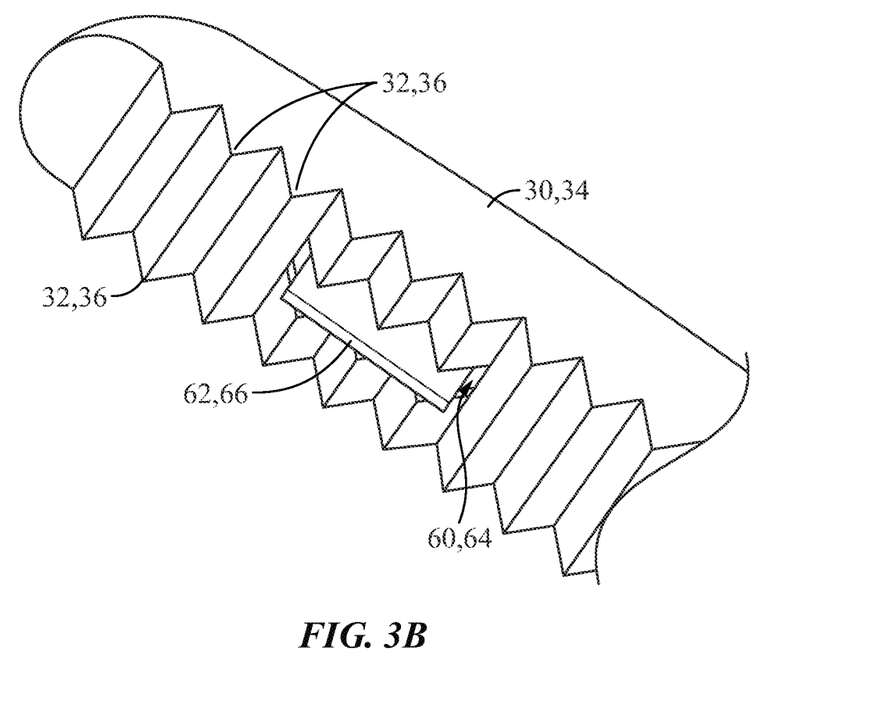
FIG. 3B shows a perspective view of the jaw in FIG. 3A with a blade protruding from the slot, according to one or more aspects.

FIGS. 3A and 3B illustrate a jaw of the scissor clamp 10, according to one or more aspects. The jaw in FIGS. 3A and 3B is representative of either or both the bottom jaw 30 and/or the top jaw 34. FIGS. 3A and 3B also illustrate the top jaw 34 and/or the bottom jaw 30, with a top slot 64 and/or a bottom slot 60. In FIG. 3A, there is no blade protruding from the top and/or bottom slots 64, 60. The top slot 64 and/or the bottom slot 60 are centered throughout the top jaw teeth 36 and/or the bottom jaw teeth 32, respectively, have the same dimensions, and/or are positioned to match the position of the other so that they face each other in the closed configuration, as described for FIG. 4C, below. According to one or more aspects, the top slot 64 and/or the bottom slot 60 are not positioned in the center, but instead positioned at the edges of the top jaw 34 and/or the bottom jaw 30, towards the top and/or bottom tips 40, 38, and/or distal from the top and/or bottom tips 40, 38, with the top slot 64 and/or the bottom slot 60 matching the position and/or dimensions of each other, partially matching the position and/or dimensions of each other, or not matching and/or dimensions the position of each other. According to one or more aspects, the bottom blade 62 and/or the top blade 66 are/is dimensioned to protrude from and/or retract into the bottom slot 60 and/or the top slot 62. According to one or more aspects, the top jaw 34 and/or the bottom jaw 30 have a plurality of slots, one slot, or no slots. Note that while FIGS. 3A and 3B are representative of the bottom jaw 30 and/or the top jaw 34, the top jaw teeth 36 and the bottom jaw teeth 32 must match the crests of one with the troughs of the other for series of the top and bottom jaw teeth 36, 32 to fit into each other and the top and bottom jaws 34, 30 to fully close.

In FIG. 3B, a top blade 66 and/or a bottom blade 62 are positioned, oriented, and/or dimensioned to fit through the top and/or bottom slots 64, 60. The top blade 66 and/or the bottom blade 62 are configured to protrude from and retract into the top and/or bottom slots 64, 60. When the top blade 66 and/or the bottom blade 62 are/is retracted, the top jaw 34 and/or the bottom jaw 30 overlap over the top blade 66 and/or the bottom blade 62, covering cutting edges of the top and/or bottom blades 66, 62, with the top and/or bottom blades 66, 62 protruding and becoming exposed within the confines of the space created by the top and/or bottom slots 64, 60 when the top jaw 34 and the bottom jaw 30 are completely brought together and the first finger ring 20 and the second finger ring 24 are moved further towards each other, as shown in FIGS. 4B and 4C. Thus, when the scissor clamp 10 is brought close to or into the surgical area of a patient, the surgeon handling the scissor clamp 10 does not have to be concerned about the top blade 66 and/or the bottom blade 62 inadvertently cutting the patient because the top blade 66 and/or the bottom blade 62 are always either retracted or protruding inside the enclosure or confines created by the the top and/or bottom slots 64, 60.

The top and/or bottom blades 66, 62 cross each other, to achieve a cutting operation such that, like scissor blades, a first side surface of one of the top and the bottom blade 66, 62 is at least partially overlapping, in close proximity to, and/or at least partially pressed against a second side surface of the other one of the bottom and the top blade 62, 66. According to one or more aspects, there are/is no top and/or bottom blades 66, 62. According to one or more aspects, a blade of a first jaw crosses with a lateral surface area of the top or bottom teeth 36, 32 and/or the top or bottom slot 64, 60 of a second jaw to cause a cutting operation. A cutting operation includes, for example, the function or process of cutting material (like a string, a suture, a medical tube, and/or the like) and/or tissue.

Figure 4A:
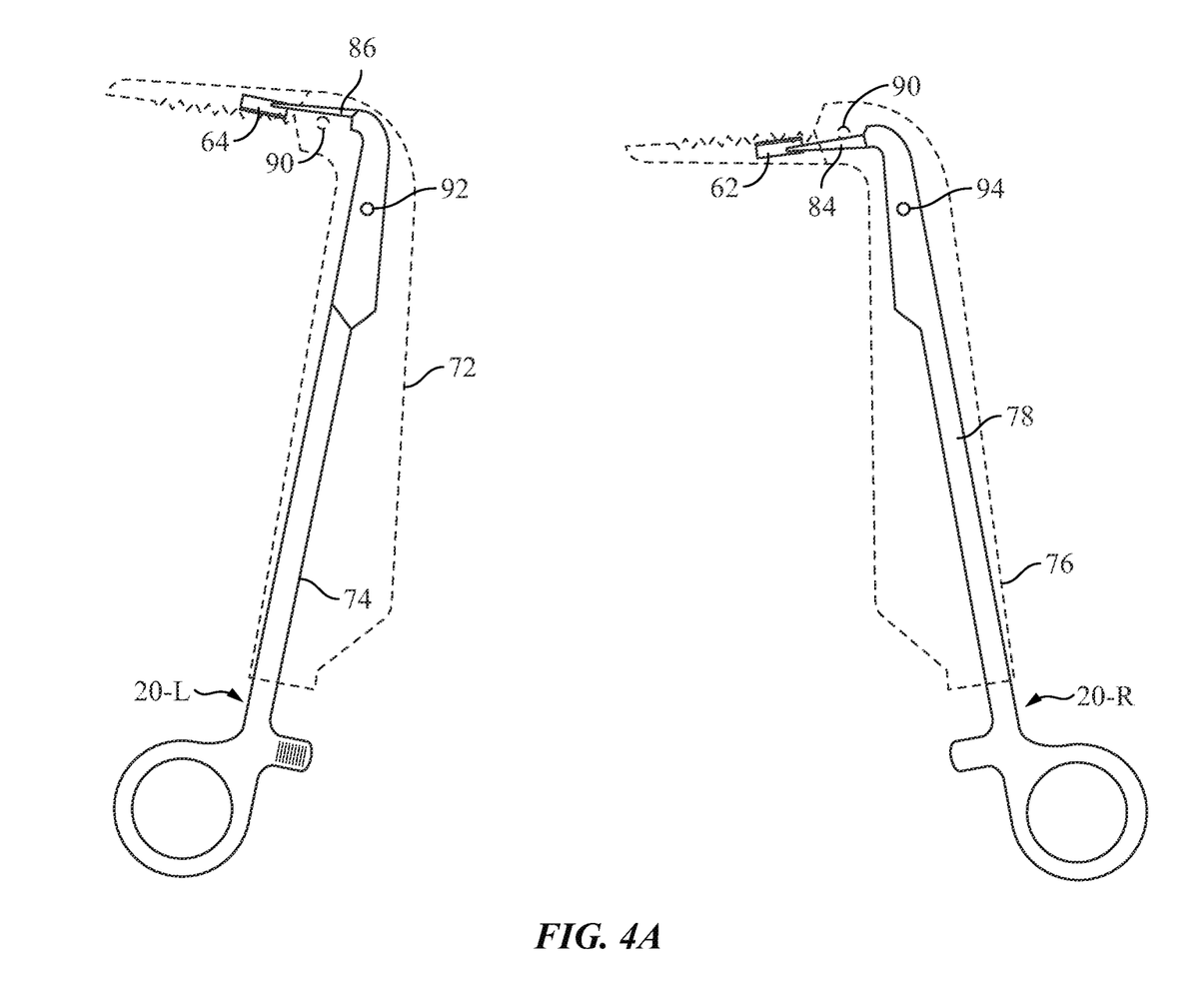
FIG. 4A shows separate double shanks of a scissor clamp with a blade retracted in each of the bottom and upper jaws, according to one or more aspects.
Figure 4B:
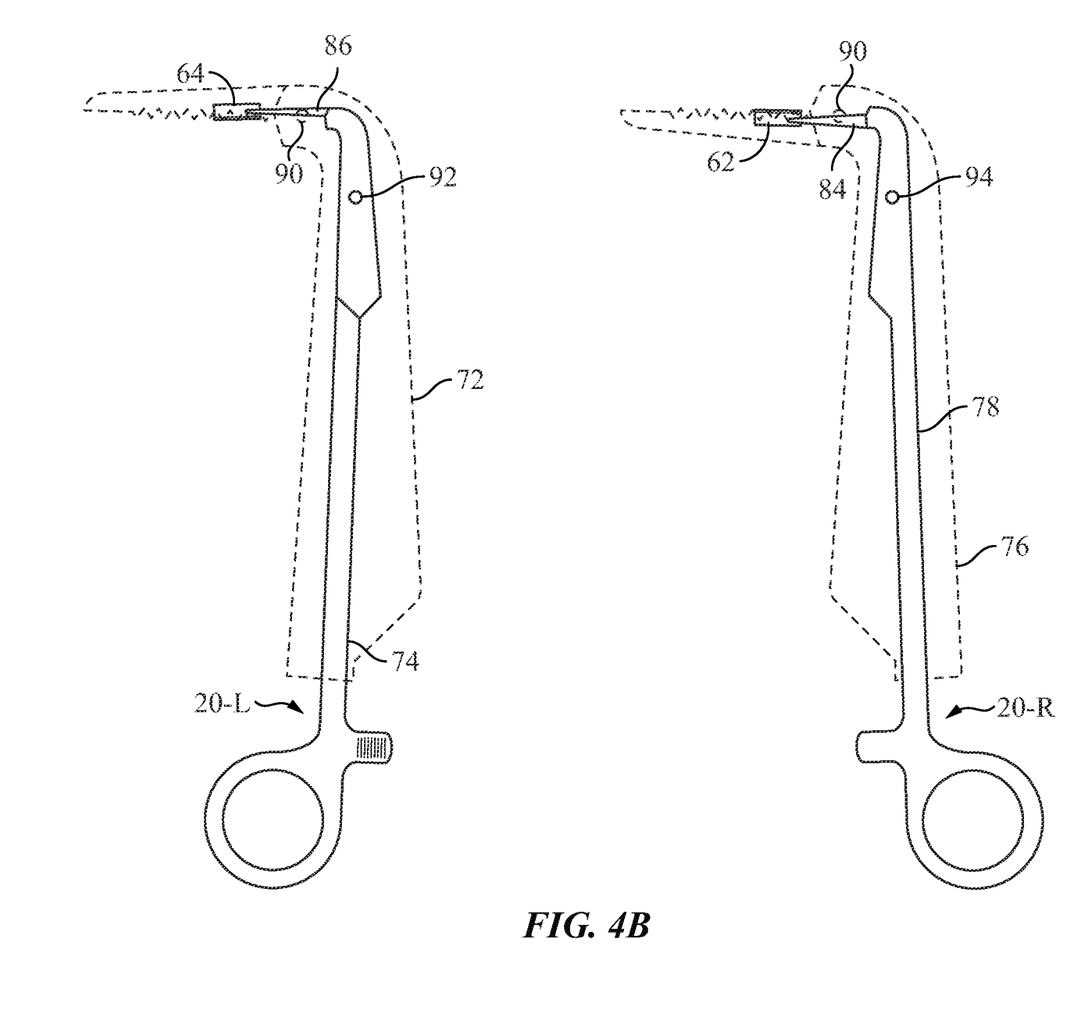
FIG. 4B shows separate double shanks of the scissor clamp of FIG. 4A with each of the blades protruding from the respective upper and lower jaws, according to one or more aspects.
Figure 4C:
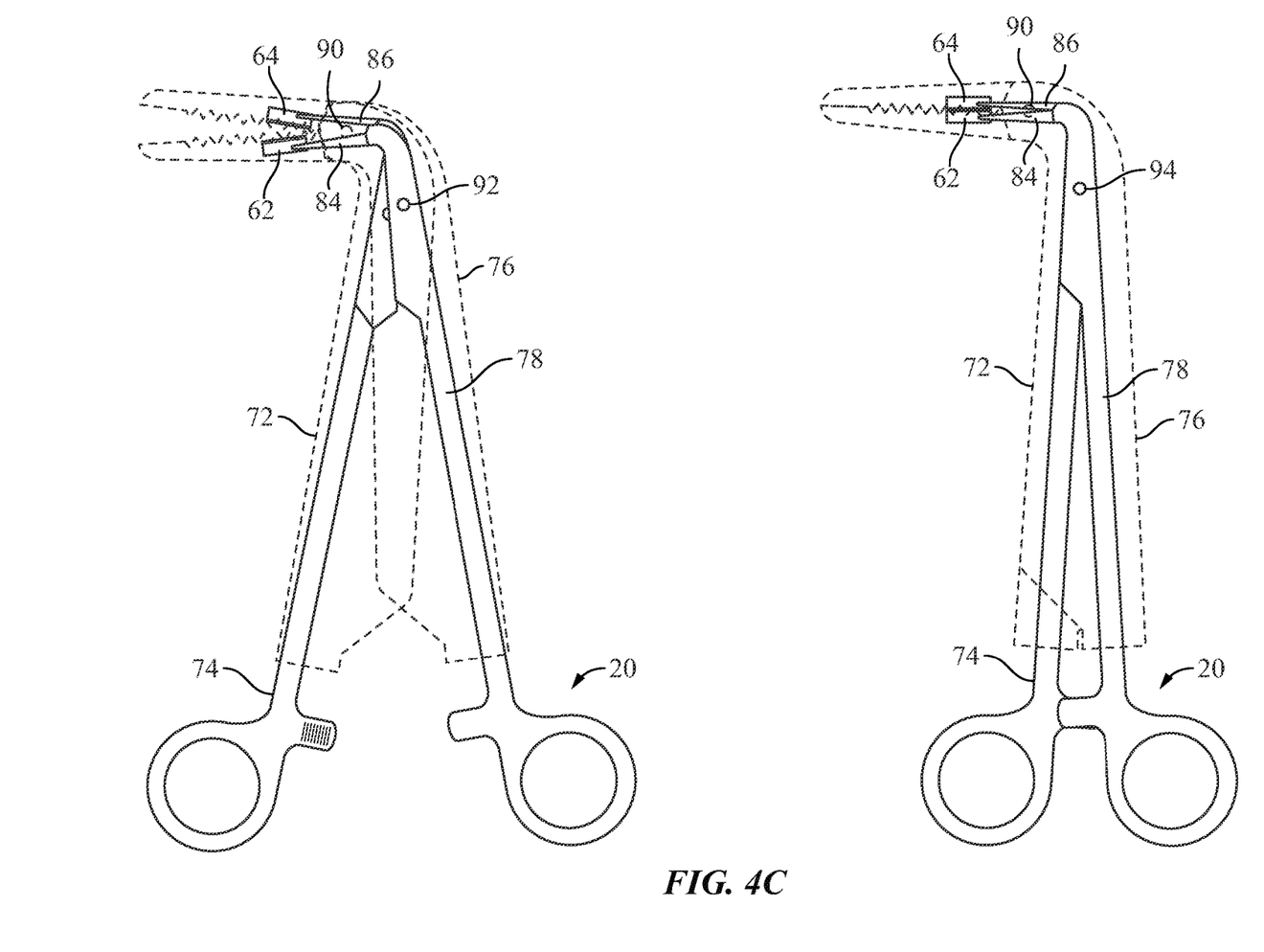
FIG. 4C shows the double shanks of the scissor clamp of FIGS. 4A and 4B in open configuration with the blades retracted and in close configuration with the blades protruding and overlapping, according to one or more aspects.

FIGS. 4A, 4B, and 4C illustrate a scissor clamp 20 which incorporates the aspects, characteristics, and features of the scissor clamp 10, FIGS. 4A and 4B show first-side scissor clamp parts 20-L and second-side scissor clamp parts 20-R separately to make aspects more apparent, while FIG. 4C shows the first-side and second-side scissor clamp parts together. In FIGS. 4A, 4B, and 4C, a first sleeve box lock 72 and a second sleeve box lock 76 are drawn without surface to show the components and aspects inside the first sleeve box lock 72 and the second sleeve box lock 76. The first and the second sleeve box locks 72 and 76 are mechanically connected by a box lock pivot 90. The rotation of the of the first and the second sleeve box locks 72 and 76 with respect to each other about the box lock pivot 90 causes the top jaw 34 and the bottom jaw 30 to open and close. FIG. 4A and the scissor clamp 20 to the left in FIG. 4C illustrate the scissor clamp 20 in open configuration. FIG. 4B and the scissor clamp 20 to the right in FIG. 4C illustrate the scissor clamp 20 in closed configuration.

Inside the first sleeve box lock 72 is a first internal shank 74. The first internal shank 74 is mechanically connected to and rotates inside the first sleeve box lock 72 about a first internal pivot 92. The first internal shank 74 has a first blade arm 84 that holds the top blade 66.

The second internal shank 78 is mechanically connected to and rotates inside the second sleeve box lock 76 about a second internal pivot 94. The second internal shank 78 has a second blade arm 86 that holds the bottom blade 62. The first sleeve box lock 72, the first internal shank 74, the second sleeve box lock 76, and/or the second internal shank 78 incorporate the aspects, characteristics, and features of the first shank 22 and/or the second shank 26. According to one or more aspects, the first internal pivot 92 is the same as the second internal pivot 94. According to one or more aspects, the first sleeve box lock 72, the first internal shank 74, the second sleeve box lock 76, and/or the second internal shank 78 share the same pivot.

When the scissor clamp 20 is in open configuration and a user starts to bring the first and the second sleeve box locks 72 and 76 together. The top blade 66 exits the top slot 64 of the top jaw 34 (as discussed for FIGS. 3A and 3B, above) towards the bottom blade 62 and the bottom blade 62 exits the bottom slot 60 of the bottom jaw 30 (as discussed for FIGS. 3A and 3B, above) towards the top blade 66 when the top jaw 34 and the bottom jaw 30 are completely brought together and the first finger ring 20 and the second finger ring 24 are moved further towards each other. Note that to cause the top blade 66 and/or the bottom blade 62 to protrude, giving way for the rotation of the first and/or the second internal shanks 72 and 76 to cause the first and/or the second blade arms 84 and 86 to move. According to one or more aspects, the top blade 66 and/or the bottom blade 62 protrude a distance from the top slot 64 and/or the bottom slot 60 based on the locking position of the ratchets 28.

According to one or more aspects, the first and second shanks 22 and 26 are configured to continue to move to produce blades after the top jaw 34 and the bottom jaw 30 are completely brought together (not shown). Note that if the top and bottom jaws 34 and 30 have tissue or other material of significant thickness between them, the top and bottom jaws 34 and 30 cannot be completely brought together and the cutting features will not operate (for example, blades advancing or cover portions retreating, as discussed above). According to one or more aspects, cutting features operate based on the locking position of the ratchets 28, regardless of whether the top and bottom jaws 34 and 30 have been brought together or have been completely brought together.

Figure 5:
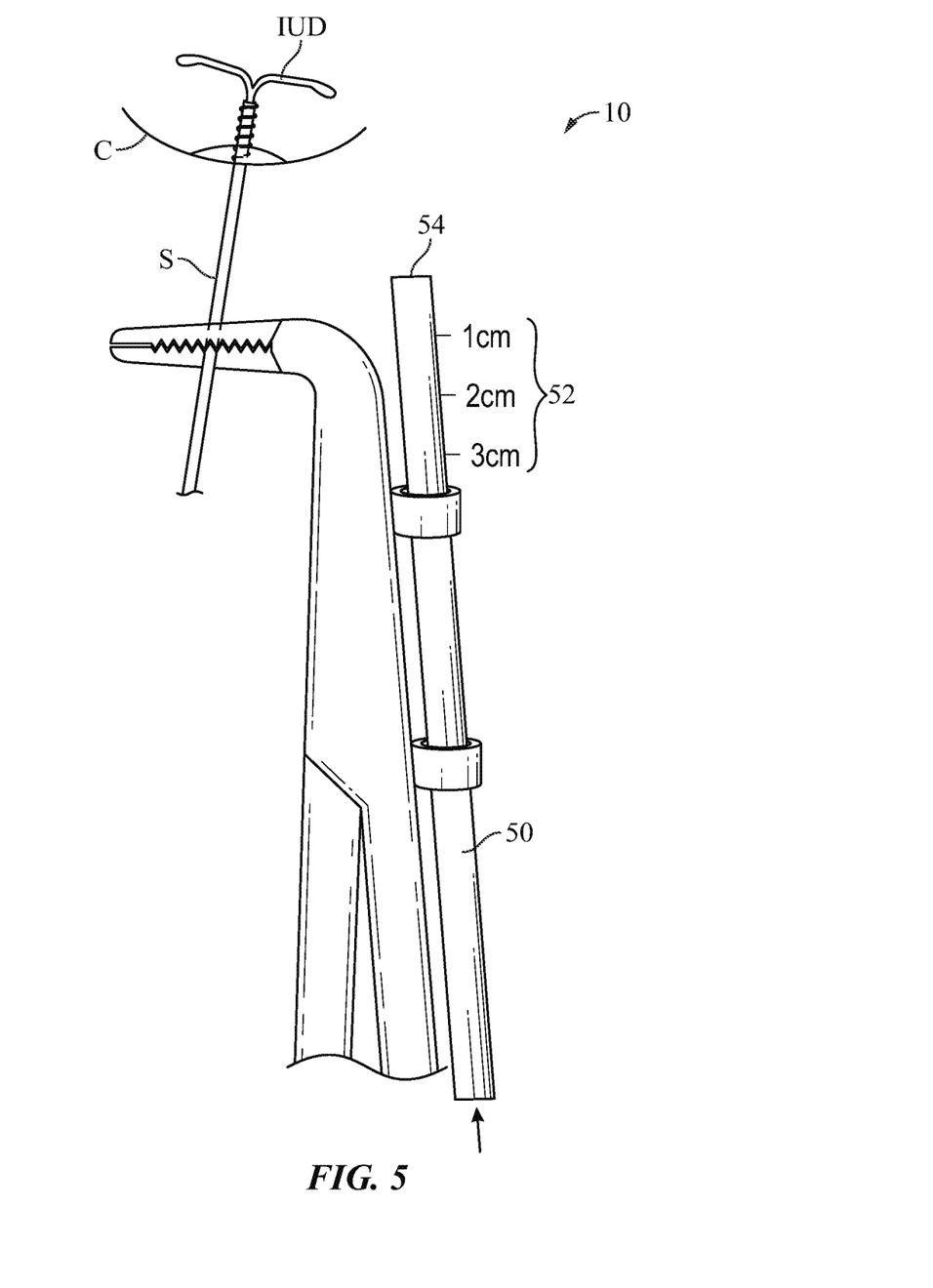
FIG. 5 shows an enlarged partial view of a suture scissor clamp in operation, according to embodiments described herein.

FIG. 5 illustrates the suture scissor clamp 10 in operation. The suture scissor clamp 10 is grasping suture strings S from an IUD at the edge of a cervix C. A tube 50, which can be a uterine sound pipette or a biopsy pipette, is inserted through the first attachment loop 42 and the second attachment loop 44. The tube 50 can also be a duct, pipe, catheter, pipette, G-tube, J-tube, and/or the like. The tube 50 has distance measurements 52 that measure the distance from the suture scissor clamp 10 to the tube distal end 54. With the distance measurements 52, the end of the tissue plane where the suture will be cut from can be accurately measured to the desired length. According to one or more aspects, the distance measurements 52 have a plurality of ridges that sound off (for example, emit a clicking sound) when moved through the first attachment loop 42 and/or the second attachment loop 44. The sound emitted from the ridges informs that the tube 50 has been moved a predetermined length. For example, the plurality of ridges could be spaced apart 0.25 centimeters from each other and configured to emit a clicking sound when moved through the one or more attachment loops (such as the first attachment loop 42 and/or the second attachment loop 44), so that every 4 clicks in one direction equals one centimeter.

All parts and components described herein are made of materials suitable for medical use. These can include metals, plastics, and/or synthetic materials, whether designed for one-time use or for repetitive use. Parts can be designed for one-time use or for frequent replacement, while other parts can be designed for repetitive use. For example, the top and/or bottom blades 66, 62 can be designed for limited use (one use or use in approximately 50 operations) and replacement, while the rest of the scissor clamp 10, 20 can be designed for continuous, repetitive use by appropriate cleaning and maintenance.

Many different embodiments have been disclosed herein, in connection with the above description and the drawings. It will be understood that it would be unduly repetitious and obfuscating to describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

An equivalent substitution of two or more elements can be made for any one of the elements in the claims below or that a single element can be substituted for two or more elements in a claim. Although elements can be described above as acting in certain combinations and even initially claimed as such, it is to be expressly understood that one or more elements from a claimed combination can in some cases be excised from the combination and that the claimed combination can be directed to a subcombination or variation of a subcombination.

It will be appreciated by persons skilled in the art that the present embodiment is not limited to what has been particularly shown and described hereinabove. A variety of modifications and variations are possible in light of the above teachings without departing from the following claims.

What is claimed is:

1. A suture scissor clamp comprising:
a first shank having a first finger ring and connected to a first jaw;
a second shank having a second finger ring and connected to a second jaw;
the first shank connected to the second shank by crossing the second shank such that when the first ring and the second ring are moved towards each other, the first jaw and the second jaw move towards each other;
a first blade connected to the first jaw; and
a second blade connected to the second jaw;
wherein the first blade and the second blade are not operable until after the first jaw and the second jaw are brought together and wherein the first blade exits the first jaw towards the second blade and the second blade exits the second jaw towards the first blade when the first jaw and the second jaw are completely brought together and the first ring and the second ring are moved further towards each other.

2. The suture scissor clamp of claim 1, wherein the first blade is inside the first jaw and the second blade is inside the second jaw.

3. The suture scissor clamp of claim 1, wherein the suture scissor clamp is manipulated between an open configuration and a closed configuration.

4. The suture scissor clamp of claim 1, wherein the suture scissor clamp is designed for ambidextrous use.

5. The suture scissor clamp of claim 1, further comprising a locking ratchet to lock the suture scissor clamp in a user-selected position.

6. The suture scissor clamp of claim 1, further comprising a plurality of top teeth protruding from a top jaw and a plurality of bottom teeth protruding from a bottom jaw.

7. The suture scissor clamp of claim 6, wherein the closed configuration is defined as having no gaps between the plurality of top teeth and the plurality of bottom teeth.

8. A suture scissor clamp comprising:
a first shank having a first finger ring and connected to a first jaw;
a second shank having a second finger ring and connected to a second jaw;
the first shank connected to the second shank by crossing the second shank such that when the first ring and the second ring are moved towards each other, the first jaw and the second jaw move towards each other;
a first blade connected to the first jaw; and
a second blade connected to the second jaw;
wherein the first blade and the second blade are not operable until after the first jaw and the second jaw are brought together, wherein the first blade is inside the first jaw and the second blade is inside the second jaw, and wherein the first blade exits the first jaw towards the second blade and the second blade exits the second jaw towards the first blade when the first jaw and the second jaw are completely brought together and the first ring and the second ring are moved further towards each other.

9. The suture scissor clamp of claim 8, wherein the suture scissor clamp is manipulated between an open configuration and a closed configuration.

10. The suture scissor clamp of claim 8, wherein the suture scissor clamp is designed for ambidextrous use.

11. The suture scissor clamp of claim 8, further comprising a locking ratchet to lock the suture scissor clamp in a user-selected position.

12. The suture scissor clamp of claim 8, further comprising a plurality of top teeth protruding from a top jaw and a plurality of bottom teeth protruding from a bottom jaw.

13. The suture scissor clamp of claim 12, wherein the closed configuration is defined as having no gaps between the plurality of top teeth and the plurality of bottom teeth.

14. The suture scissor clamp of claim 8, further comprising a bottom tip positioned on a bottom jaw having a bottom blade portion confined to an inside of the suture scissor clamp.

15. The suture scissor clamp of claim 8, further comprising a top tip positioned on a top jaw having a top blade portion confined to an inside of the suture scissor clamp.

16. The suture scissor clamp of claim 8, further comprising a top slot having no blade protruding therefrom, wherein the top slot is centered throughout one or more top jaw teeth.

17. The suture scissor clamp of claim 8, further comprising a bottom slot having no blade protruding therefrom, wherein the bottom slot is centered throughout one or more bottom jaw teeth.

* * * * *